US012070481B2

(12) United States Patent
Gokaraju et al.

(10) Patent No.: US 12,070,481 B2
(45) Date of Patent: Aug. 27, 2024

(54) COMPOSITIONS FOR IMPROVING LEAN BODY MASS, BROWN ADIPOSE TISSUE AND FOR INHIBITING ADVANCED GLYCATION ENDS PRODUCT

(71) Applicants: LAILA NUTRACEUTICALS, Vijayawada (IN); P.L. THOMAS-LAILA NUTRACEUTICALS, INC., Morristown, NJ (US)

(72) Inventors: Ganga Raju Gokaraju, Vijaywada (IN); Rama Raju Gokaraju, Vijayawada (IN); Trimurtulu Golakoti, Vijayawada (IN); Venkateswara Rao Chirravuri, Vijayawada (IN); Venkateswarlu Somepalli, Vijayawada (IN); Kiran Bhupathiraju, Vijayawada (IN)

(73) Assignees: LAILA NUTRACEUTICALS, Vijayawada (IN); P.L. THOMAS-LAILA NUTRACEUTICALS, Morristown, NJ (US)

( * ) Notice: Subject to any disclaimer, the term of this patent is extended or adjusted under 35 U.S.C. 154(b) by 0 days.

(21) Appl. No.: 16/756,757

(22) PCT Filed: Oct. 16, 2018

(86) PCT No.: PCT/IN2018/050668
§ 371 (c)(1),
(2) Date: Apr. 16, 2020

(87) PCT Pub. No.: WO2019/077629
PCT Pub. Date: Apr. 25, 2019

(65) Prior Publication Data
US 2020/0330544 A1    Oct. 22, 2020

(30) Foreign Application Priority Data
Oct. 16, 2017  (IN) ............................. 201741029057

(51) Int. Cl.
*A61K 36/9066* (2006.01)
*A23L 33/105* (2016.01)
*A61K 9/16* (2006.01)
*A61K 36/75* (2006.01)

(52) U.S. Cl.
CPC ........ *A61K 36/9066* (2013.01); *A23L 33/105* (2016.08); *A61K 36/75* (2013.01); *A61K 9/16* (2013.01)

(58) Field of Classification Search
None
See application file for complete search history.

(56) References Cited

U.S. PATENT DOCUMENTS

| 8,541,383 B2* | 9/2013 | Gokaraju ................ A61P 35/00 514/27 |
| 9,420,808 B2 | 8/2016 | Yamka et al. |
| 2004/0023889 A1 | 2/2004 | Gardiner et al. |
| 2012/0031785 A1 | 2/2012 | Yamka et al. |
| 2017/0182107 A1 | 6/2017 | Kim |

FOREIGN PATENT DOCUMENTS

EP          2 500 361 B1      3/2016

OTHER PUBLICATIONS

Siepmann et al., Journal of Controlled release, 125, 2008, pp. 1-15.*
Bioactives, 3 pages.*
Vlassara et al., NIH public access, Curr. Diab. Rep. Jan. 2014, 14(1): 453.*
Dixit, et al., "Efficacy of a novel herbal formulation for weight loss demonstrated in a 16-week randomized, double-blind, placebo-controlled clinical trial with healthy overweight adults. Short Title: Clinical efficacy of an herbal blend in overweight adults", Diabetes Obesity and Metabolism, vol. 20, Issue 11, 31 pages. (Jun. 19, 2018).
Lin, et al., "Curcumin inhibits gene expression of receptor for advanced glycation endproducts (RAGE) in hepatic stellate cells in vitro by elevating PPAR gama activity and attenuating oxidative stress", British Journal of Pharmacology, 166, pp. 2212-2227. (2012).
Sangkitikomol, et al., "Effect of Moringa oleifera on advanced glycation end-product formation and lipid metabolism gene expression in HepG2 cells", Genetics and Molecular Research, 13 (1), pp. 723-735. (2014).
Sengupta, et al., "Efficacy and tolerability of a novel herbal formulation for weight management in obese subjects: a randomized double blind placebo controlled clinical study", Lipids in Health and Disease, 11:122, 10 pages. (2012).
Wang, et al., "Curcumin promotes browning of white adipose tissue in a norepinephrine-dependent way", Biochemical and Biophysical Research Communications, pp. 1-7. (2015).

(Continued)

*Primary Examiner* — Michael V Meller
(74) *Attorney, Agent, or Firm* — Kramer & Amado, P.C.

(57) ABSTRACT

Synergistic herbal compositions comprising combination of extracts, fractions or phytochemicals or mixtures thereof derived from *Moringa oleifera*, *Murraya koenigii* and *Curcuma longa* for increasing lean body mass and brown adipose tissue; for accelerating the conversion of the white adipose tissue (WAT) to brown adipose tissue (BAT), inhibiting excessive generation of advanced glycation end (AGE) products and disease conditions associated with increased levels of advanced glycation end (AGE) products. The invention further provides a method of increasing lean body mass and brown adipose tissue; accelerating the conversion of the white adipose tissue (WAT) to brown adipose tissue (BAT), inhibiting excessive generation of advanced glycation end (AGE) products and disease conditions associated with increased levels of advanced glycation end (AGE) products in mammals.

21 Claims, 2 Drawing Sheets

(56) References Cited

OTHER PUBLICATIONS

EPO Extended Search Report re: 18869180.2-1112 / 3697427 PCT/IN2018050661 dated Jun. 28, 2021; 1 pg.
Supplementary European Search Report re: Application No. 18 869 180; Jun. 17, 2021; 1 pg.
I. Barbagallo, et al., "*Moringa oleifera* lam. Improves Lipid Metabolism During Adipogenic Differentiation of Human Stem Cells," European Review for Medical and Pharmacological Sciences; 2016; 10 pgs.
Ibrar Khan, et al., "Anti-glycationand Anti-oxidation Properties of Capsicum Frutescens and Curcuma Longa Fruits: Possible Role in Prevention of Diabetic Complication," Pak. J. Pharm. Scl., vol. 27, No. 5, Sep. 2014, pp. 1359-1362; 5 pgs.

* cited by examiner

COMPOSITIONS FOR IMPROVING LEAN BODY MASS, BROWN ADIPOSE TISSUE AND FOR INHIBITING ADVANCED GLYCATION ENDS PRODUCT

TECHNICAL FIELD OF THE INVENTION

The present invention relates to a synergistic composition comprising combination of extracts or fractions or phytochemicals or mixtures thereof derived from *Moringa oleifera, Murraya koenigii* and *Curcuma longa* for increasing lean body mass and brown adipose tissue; for accelerating the conversion of white adipose tissue (WAT) to brown adipose tissue (WAT); inhibiting excessive generation of advanced glycation end (AGE) products and treating the disease condition associated with advanced glycation end (AGE) products. The present invention further relates to a method of increasing lean body mass and brown adipose tissue; method of converting the white adipose tissue (WAT) to brown adipose tissue (WAT); method of inhibiting excessive generation of advanced glycation end (AGE) products and treating the disease condition associated with advanced glycation end (AGE) products in mammals by supplementing mammal in need with the said synergistic composition.

BACKGROUND OF THE INVENTION

Lean body mass is the amount of muscle in the body independent of fat, bone and other parts. Food supplements based on protein, aminoacids and micronutrients and other approaches for gaining muscle mass have become very popular among athletes and bodybuilders. As athletes continually strive for improved performance, there is a continuing need for newer and more effective supplements to aid in increasing lean body mass, muscle size and/or strength.

Adipose tissue, though best known for its role in fat storage, can also suppress weight gain and metabolic disease through the action of specialized, heat-producing adipocytes. These are called Brown adipocytes, which are located in dedicated depots and express constitutively high levels of thermogenic genes. In addition, there is another form called inducible 'brown-like' adipocytes, also known as beige cells, which develop in white fat in response to various activators. The brown and beige fat cells reduce metabolic disease and correlate with leanness in humans.

Many genes and pathways that regulate brown and beige adipocyte biology have now been identified, providing a variety of promising therapeutic targets for metabolic disease.

Advanced glycation end products (AGEs), also known as glycotoxins, are a diverse group of highly active oxidant compounds, formed by a non-enzymatic reaction between reducing sugars and free amino groups of proteins, lipids, or nucleic acids and this reaction is known as Maillard or browning reaction. AGEs are formed during normal metabolism and they become pathogenic if high levels of AGEs are accumulated in tissues and the circulation. The AGEs play a role in the development and worsening of complications of diabetes, atherosclerosis, normal aging process, arthritis, cancer and progression of age-related neurodegenerative diseases like Alzheimer's disease.

US2004023889A1 discloses Food supplement compositions comprise alpha lipoic acid or a derivative thereof, and an amino acid. US'889 further discloses methods of use of the aforementioned composition in increasing lean mass and/or muscle size and/or strength in individuals, particularly, athletes.

US20040077556 A1 discloses composition for promoting weight loss, thermogenesis, increasing metabolism, boosting energy levels, promoting appetite suppression, for promoting lean muscle mass in mammals comprising effective amounts of: epigallocatechin gallate; caffeine; and 1-tyrosine.

U.S. Pat. No. 9,420,808B2 discloses compositions and methods for increasing lean muscle mass and/or reducing fat gain in growing animals by feeding the animals a composition having a total lysine to metabolizable energy ratio of from about 2.5 to about 6 g/Mcal and comprising (a) arginine in a total arginine to total lysine ratio of from about 1.1 to about 1.6; (b) isoleucine in a total isoleucine to total lysine ratio of from about 0.8 to about 1.3; (c) leucine in a total leucine to total lysine ratio of from about 1.8 to about 3.0; (d) valine in a total valine to total lysine ratio of from about 0.8 to about 1.4; and (e) methionine and cystine in a total methionine plus cystine to total lysine ratio of from about 0.8 to about 1.7.

EP2500361B1 discloses isolated proteins, particularly monoclonal antibodies, in particular CDR-grafted, humanized antibodies which bind to RAGE protein. Specifically, these antibodies have the ability to inhibit the binding of RAGE to its various ligands.

US2017182107A1 discloses a composition of cinnamon twig and moutan root bark, cinnamon twig and peony root, or cinnamon twig and poria for the inhibition of excessive generation of advanced glycation end-products, which occurs under chronic diabetic conditions, exhibit the effect of fragmentizing a cross-link between the advanced glycation end-products and matrix proteins.

U.S. Pat. No. 8,541,383 B2 discloses a Synergistic antiadipogenic and pro-lipolytic compositions for the prevention and amelioration of adipogenesis and lipolysis mediated diseases, comprising at least two extracts selected from enriched demethylated curcuminoids obtained from *Curcuma longa, Moringa oleifera* and *Murraya koenigii*. However, US'383 is silent on supplements that inhibits excessive generation of advanced glycation end products and increases lean muscle mass and brown adipose tissue.

To the best of the inventors knowledge, the compositions containing the extracts derived from *Moringa oleifera, Murraya koenigii* and *Curcuma longa* for inhibition of excessive generation of advanced glycation end (AGE) products and increasing lean body mass and brown adipose tissue are not disclosed in the prior art.

So there remains a continues need in the art to provide safer natural supplements for the inhibition of excessive generation of advanced glycation end products, increasing lean body mass and brown adipose tissue (BAT); and converting the white adipose tissue (WAT) to brown adipose tissue (WAT).

OBJECT OF THE INVENTION

Therefore the principle object of the present invention is to provide a synergistic composition comprising combination of extracts or fractions or phytochemicals or mixtures thereof derived from *Moringa oleifera, Murraya koenigii* and *Curcuma longa* for increasing lean body mass and brown adipose tissue; for accelerating the conversion of the white adipose tissue (WAT) to brown adipose tissue (WAT); for inhibiting excessive generation of advanced glycation end (AGE) products and treating the disease conditions associated with advanced glycation end (AGE) products.

Another object of the present invention is to provide a method of increasing lean body mass and brown adipose tissue; method of converting the white adipose tissue (WAT) to brown adipose tissue (WAT); method of inhibiting excessive generation of advanced glycation end (AGE) products and treating the disease condition associated with advanced glycation end (AGE) products in mammals by supplementing mammal in need with a suitable dose of a synergistic composition comprising extracts or fractions or phytochemicals or mixtures thereof derived from *Moringa oleifera, Murraya koenigii* and *Curcuma longa*.

SUMMARY OF THE INVENTION

In meeting the above objectives, the present invention provides a synergistic composition comprising combination of extracts or fractions or phytochemicals or mixtures thereof derived from *Moringa oleifera, Murraya koenigii* and *Curcuma longa* for increasing lean body mass and brown adipose tissue; for accelerating the conversion of the white adipose tissue (WAT) to brown adipose tissue (WAT); inhibiting excessive generation of advanced glycation end (AGE) products and treating the disease condition associated with advanced glycation end (AGE) products.

Yet another aspect of the invention provides a method of increasing lean body mass and brown adipose tissue; method of accelerating the conversion of white adipose tissue (WAT) to brown adipose tissue (WAT) in mammals wherein the method comprises supplementing mammals with an effective dose of a synergistic composition comprising combination of extracts or fractions or phytochemicals or mixtures thereof derived from *Moringa oleifera, Murraya koenigii* and *Curcuma longa* and optionally containing at least one additional ingredient selected from pharmaceutically, nutraceutically and dietically acceptable excipient, diluent and carrier.

Yet another aspect of the invention provides a method of inhibiting excessive generation of advanced glycation end (AGE) products and treating the disease condition associated with advanced glycation end (AGE) products in mammals wherein the method comprises supplementing mammals with an effective dose of a synergistic composition comprising combination of extracts or fractions or phytochemicals or mixtures thereof derived from *Moringa oleifera, Murraya koenigii* and *Curcuma longa* and optionally containing at least one additional ingredient selected from pharmaceutically, nutraceutically and dietically acceptable excipient, diluent, and carrier.

DETAILED DESCRIPTION OF THE INVENTION

Figure 1:
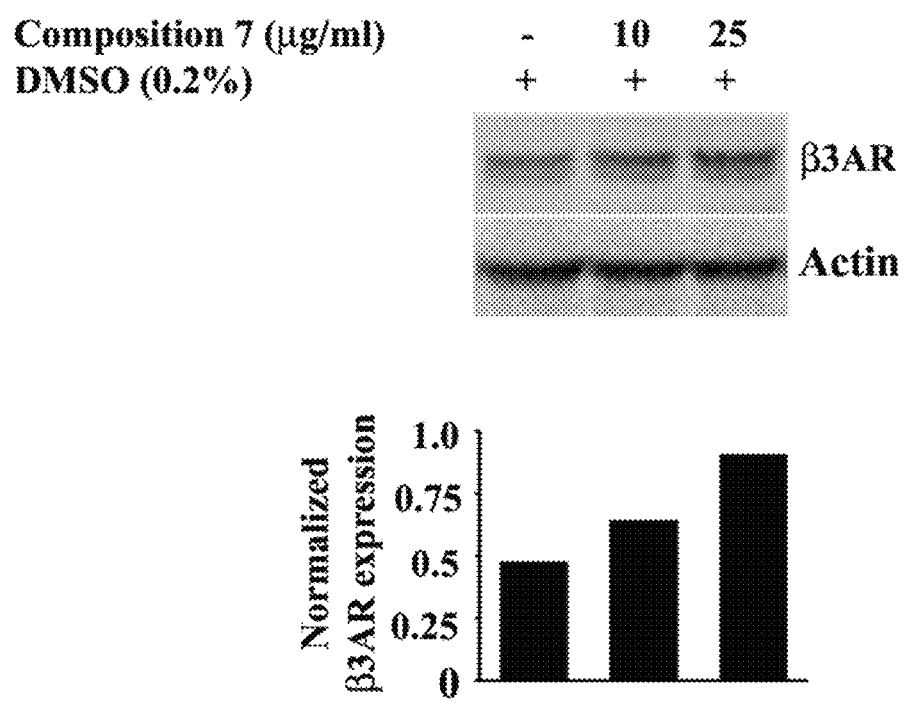
FIG. 1: Representative immunoblot indicates that Composition-7 overexpresses β3AR protein in 3T3-L1 adipocytes. Expression of actin protein was considered as the loading control. β3AR protein expression was measured densitometrically and normalized with actin expression. The bar diagram represents the normalized levels of β3AR protein in control and Composition-7 (10 μg and 25 μg/mL) treated cells.
Figure 2A:
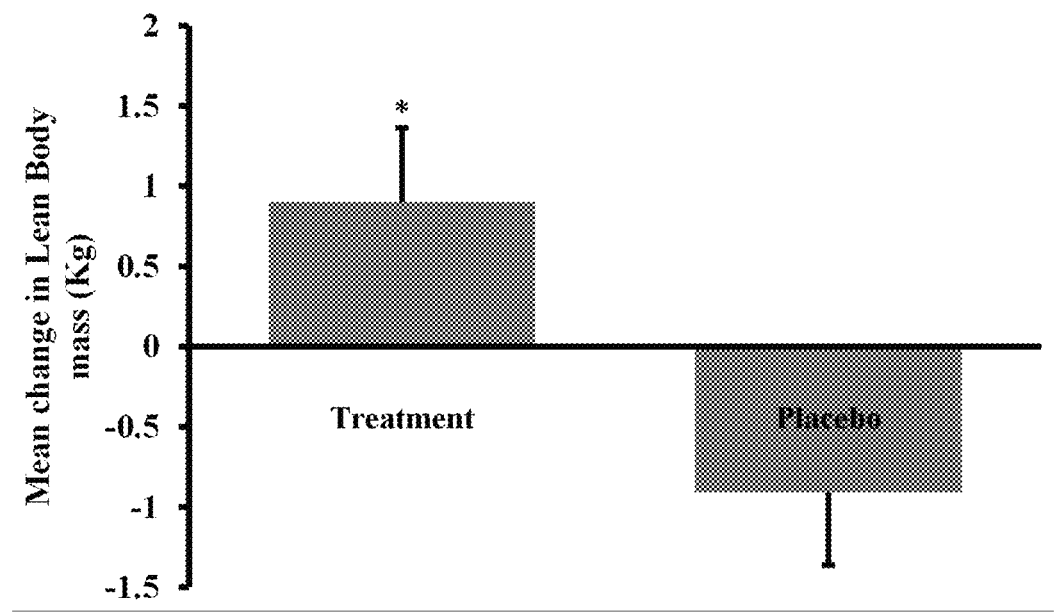
FIGS. 2A and 2B represent the mean change in lean body mass (FIG. 2A) and mean change in fat body mass (FIG. 2B) respectively in subjects treated with Composition-7 and placebo.
Figure 2B:
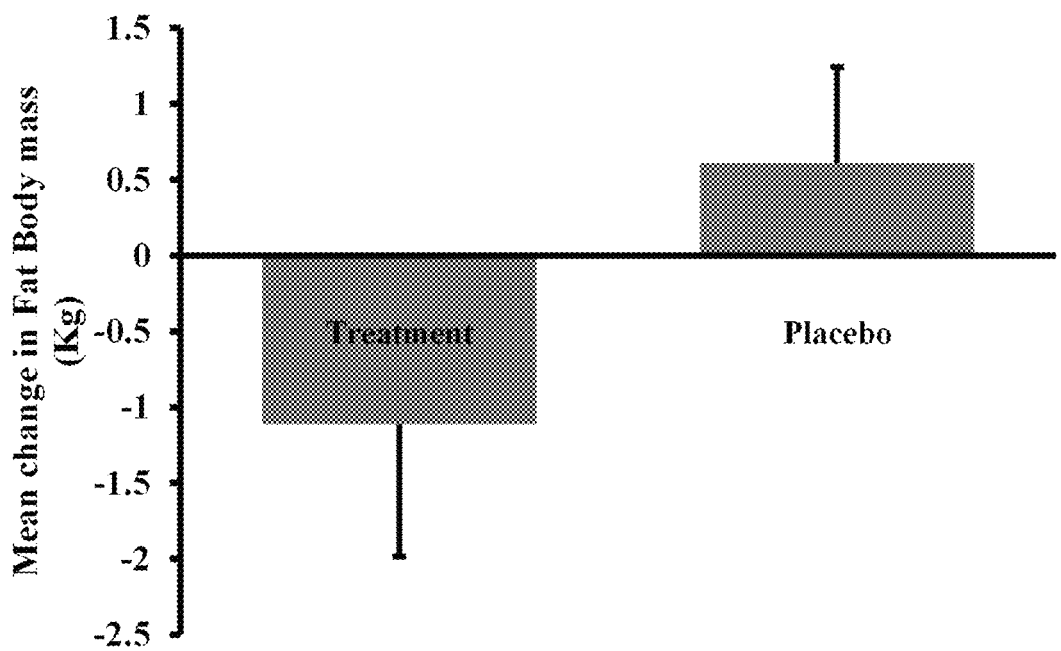

The invention will now be described in detail in connection with certain preferred and optional embodiments, so that various aspects thereof may be more fully understood and appreciated.

Lean body mass is a component of body composition independent of fat. It is obtained by subtracting body fat weight from total body weight. Food supplements based on herbal extracts for gaining muscle mass without the addition of fat have become popular among athletes and bodybuilders.

Brown Adipose Tissue:

Adipose tissue (body fat) is a loosely bound connective tissue composed of adipocytes, which are derived from pre-adipocytes. In humans, adipose tissue is located mainly beneath the skin (subcutaneous fat) and around internal organs (visceral fat). White adipose tissue (WAT), also called as white fat, is one of the two types of adipose tissue found in mammals. The other kind of adipose tissue is Brown Adipose Tissue (BAT). White adipose tissue stores energy in the form of lipids and it undergoes pathological expansion during obesity. Brown adipose tissue (BAT) is a specialized form of adipose tissue in humans and other mammals. BAT evolved in mammals to dissipate large amounts of chemical energy as heat through a process called thermogenesis. Brown fat cells possess large numbers of mitochondria, which are equipped with a specialized protein known as uncoupling protein 1 (UCP1). UCP1 short-circuits the electron transport chain, which is otherwise normally used to drive the synthesis of cellular ATP, and allowing mitochondrial membrane potential to be transduced to heat, thus making BAT a tissue capable of altering energy expenditure and fuel metabolism in mammals without an increase in physical activity. Release of catecholamines from sympathetic nerves results in UCP1 activation that stimulate proliferation and heat production by brown fat cells. In addition, brown adipose tissue contains β3 receptor, which plays a crucial role in lipolysis and thermogenesis upon activation. Therefore, a β3-AR agonist can stimulate human BAT thermogenesis and may be a promising treatment for metabolic disease.

Beige Fat and WAT Browning:

In recent years, the topic of brown adipose tissue has been reinvigorated with many new studies pertaining to brown adipose tissue differentiation, function and therapeutic promise. WAT from certain depots, in response to appropriate stimuli, can undergo a process known as "browning" where it takes on characteristics of BAT, by increasing specific protein expression such as UCP1, the presence of multilocular lipid droplets and multiple mitochondria. Peroxisome Proliferator Activated Receptor gamma co-activator 1 alpha (PGC 1α) is also one of the important regulator of transcription central to WAT browning. The fibroblast growth factor 21 (FGF21) plays a physiologic role in thermogenic recruitment of WATs and it is also an important regulator of browning. FGF21 is a hormone secreted mainly by liver. Growing body of evidence suggests that FGF21 is involved in the thermogenic functions of brown adipose tissue. Adipose-derived FGF21 acts in an autocrine/paracrine manner to increase expression of UCP1 and other thermogenic genes in fat tissues. FGF21 also enhances PGC 1α levels in fat tissues.

Advanced glycation end products (AGEs), also known as glycotoxins, formed by a non-enzymatic reaction between reducing sugars and free amino groups of proteins, lipids, or nucleic acids and they accumulate during normal aging. Accumulations of AGEs accelerate the multisystem functional decline that occurs with aging, and therefore contribute to the aging phenotype. The increased rate of accumulation of AGEs during hyperglycemia is implicated in the development of long-term complications of diabetes, including but not limited to retinopathy, nephropathy, neuropathy, atherosclerosis, and cardiovascular disease. In addition, AGE formation has been implicated in a number of other pathologies, such as, arthritis, connective tissue disease, amyloidosis, and neurodegenerative amyloid diseases, such as Alzheimer's.

Source of the herbs used in the invention as follows:
1. *Moringa oleifera* collected from Undavalli village, Undavalli panchayat, Tadepalli mandal Guntur district, Andhra Pradesh and which is cultivated.
2. *Murraya koenigii* collected from Malkapuram village, Malkapuram, Eluru mandal, West godavari district, Andhra Pradesh and which is cultivated.
3. *Curcuma longa* collected from Kunchenapalli village, Kunchenapalli panchayat, Tadepalli mandal, Guntur district, Andhra Pradesh and which is cultivated.

The inventors of the present invention have screened several herbal extracts and their compositions for their efficacy in inhibiting the formation of advanced glycation end products and found that the extracts derived from *Moringa oleifera, Murraya koenigii* and *Curcuma longa* have excellent efficacy in inhibiting the formation of Advanced Glycation End products (AGEs). In addition, the compositions comprising combination of extracts derived from *Moringa oleifera, Murraya koenigii* and *Curcuma longa* showed better efficacy in inhibiting the AGE formation compared to the effects shown by the individual ingredients as summarized in Table 5.

For example, *Moringa oleifera* 75% aqueous ethanol extract (M.O-3) at 0.6 µg/mL showed 4.26% inhibition of AGE formation; *Murraya koenigii* 60% aqueous ethanol extract (M.K-2) at 0.3 µg/mL showed 8.70% inhibition of AGE formation and *Curcuma longa* extract standardized to 95% total curcuminoids (C.L-1) at 0.1 µg/mL showed 5.47% inhibition of AGE formation. The composition-1 (C-1) containing these three extracts at 6:3:1 ratio showed 50.49% inhibition of AGE formation at 1 µg/mL concentration, which is significantly better than the additive effect (4.26%+8.70%+5.47=18.43%) from these three ingredients, suggesting synergistic inhibition of AGE formation by *Moringa oleifera* 75% aqueous ethanol extract (M.O-3), *Murraya koenigii* aqueous 60% ethanol extract (M.K-2) and *Curcuma longa* extract standardized to 95% total curcuminoids (C.L-1). These three ingredients also showed synergism when combined at ratios, 8:1:1, 4:5:1, 2:2:1, 3:6:1 and 6:3.5:0.5 as shown by the superior inhibition of AGE formation exhibited by the compositions-2, 3, 4, 5 and 6 respectively as summarized in Table 5.

Similarly, *Moringa oleifera* 90% aqueous ethanol extract (M.O-2) at 0.6 µg/mL showed 17.32% inhibition of AGE formation; *Murraya koenigii* aqueous 60% ethanol extract (M.K-2) at 0.3 µg/mL showed 8.70% inhibition of AGE formation and *Curcuma longa* extract standardized to 95% total curcuminoids (C.L-1) at 0.1 µg/mL showed 5.47% inhibition of AGE formation. The composition-7 containing these three extracts at 6:3:1 ratio showed 72.70% inhibition of AGE formation at 1 µg/mL concentration, which is significantly better than the additive effect (17.32%+8.70%+5.47=31.49%) from these three ingredients, suggesting synergistic effect in inhibition of AGE formation by *Moringa oleifera* 90% aqueous ethanol extract (M.O-2), *Murraya koenigii* aqueous 60% ethanol extract (M.K-2) and *Curcuma longa* extract standardized to 95% total curcuminoids (C.L-1). The compositions containing other solvent extracts of these herbs also showed synergistic inhibition of AGEs as summarized in Table 5.

RAGE is a receptor for AGE and EN RAGE (Extracellular newly identified RAGE-binding protein) is its natural pro-inflammatory ligand. For binding AGEs to its receptors (RAGE), EN RAGE is required. Hence modulation of EN RAGE protein ultimately affects the binding of AGEs to its receptor (RAGE). It was also reported in the prior art that AGE induces the production of Interleukin-6 (IL-6) and Interleukin-8 (IL-8); and these pro-inflammatory cytokines, in turn increase the levels of EN-RAGE protein. The inventors of the present invention evaluated the pooled sample of human serum samples obtained from the subjects supplemented with composition-7 as part of clinical study for the modulation of EN RAGE, IL6 and IL8. Interestingly, it was found that the composition-7 significantly down regulated the serum EN RAGE, IL6 and IL8 levels compared to those in the placebo treated subjects and the results are summarized in Table 6.

The inventors of the present invention have also evaluated potential of *Moringa oleifera, Murraya koenigii* and *Curcuma longa* extracts and their compositions for increasing lean body mass and brown adipose tissue; for accelerating the conversion of the white adipose tissue (WAT) to brown adipose tissue (BAT) using cellular assays for increasing specific protein expression such as uncoupling protein 1 (UCP1) and increase of fibroblast growth factor 21 (FGF21). The mouse 3T3-L1 pre-adipocytes cells treated with the compositions C-1 to C-16 showed significant improvement in the expression of UCP1 as shown by the increase in the band intensities in Western blot assay for the cell lysate solution. The efficacy of test samples expressed as UCP1 expression index, which is a ratio between the band intensity of the test sample and that of the β-Actin is summarized in Table 3. For example, the composition-1 (C-1) containing *Moringa oleifera* aqueous 75% ethanol extract (M.O-3), *Murraya koenigii* 60% aqueous ethanol extract (M.K-2) and *Curcuma longa* extract standardized to 95% total curcuminoids (C.L-1) at 6:3:1 ratio showed an UCP1 expression index of 0.928 compared to 0.60 shown by the control treated cells. This is closely 50% increase in expression index. Similarly, the composition-7 (C-7) containing *Moringa oleifera* aqueous 90% ethanol extract (M.O-3), *Murraya koenigii* 60% aqueous ethanol extract (M.K-2) and *Curcuma longa* extract standardized to 95% total curcuminoids (C.L-1) at 6:3:1 ratio showed an UCP1 expression index of 0.886. The expression data for other compositions is summarized in Table 3.

Earlier studies revealed that peroxisome proliferator activated receptor γ coactivator 1α (PGC1α) regulates thermogenesis by directly inducing the expression of UCP. In addition, FGF21 is known to increase the expression of both UCP1 and PGC1α. Hence, FGF21 has a role in the conversion of white adipose tissue (WAT) into brown adipose tissue (BAT), thermogenesis and increasing lean body mass. Hence, the inventors have screened the extracts of *Moringa oleifera, Murraya koenigii* and *Curcuma longa* and their compositions for modulation of FGF21 in cellular assays using mouse 3T3-L1 pre-adipocytes. Unexpectedly, the compositions containing above extracts have shown better improvement in FGF21 levels compared to the corresponding individual ingredients. For example, *Moringa oleifera* 75% aqueous ethanol extract (M.O-3) at 3.0 µg/mL showed 22.71% increase of FGF21; *Murraya koenigii* 60% aqueous ethanol extract (M.K-2) at 1.5 µg/mL showed 0.73% increase of FGF21 and *Curcuma longa* extract standardized to 95% total curcuminoids (C.L-1) at 0.5 µg/mL showed 3.03% increase of FGF21. The composition-1 containing these three extracts at 6:3:1 ratio showed 34.62% increase of FGF21 at 5 µg/mL concentration, which is significantly better than the additive effect (22.71%+0.73%+

3.03%=26.47%) from these three ingredients, suggesting synergistic effect by *Moringa oleifera* aqueous 75% ethanol extract (M.O-3), *Murraya koenigii* aqueous 60% ethanol extract (M.K-2) and *Curcuma longa* extract standardized to 95% total curcuminoids (C.L-1) in increasing FGF21. These three ingredients also showed synergism when combined at ratios, 8:1:1, 4:5:1, 2:2:1, 3:6:1 and 6:3.5:0.5 as shown by the superior improvement in FGF21 levels exhibited by the compositions-2, 3, 4, 5 and 6 respectively as summarized in Table 4.

Similarly, *Moringa oleifera* aqueous 90% ethanol extract (M.O-2) at 3.0 µg/mL showed 23.45% increase of FGF21; *Murraya koenigii* aqueous 60% ethanol extract (M.K-2) at 1.5 µg/mL showed 0.73% increase of FGF21 and *Curcuma longa* extract standardized to 95% total curcuminoids (C.L-1) at 0.5 µg/mL showed 3.03% increase of FGF21. The composition-7 containing these three extracts at 6:3:1 ratio showed 35.23% increase of FGF21 at 5 µg/mL concentration, which is significantly better than the additive effect (23.45%+0.73%+3.03%=27.21%) from these three ingredients, suggesting synergistic effect from *Moringa oleifera* 90% aqueous ethanol extract (M.O-2), *Murraya koenigii* 60% aqueous ethanol extract (M.K-2) and *Curcuma longa* extract standardized to 95% total curcuminoids (C.L-1) in increasing FGF21. The compositions containing other solvent extracts of these herbs also showed synergistic improvement in FGF21 levels as summarized in Table 4.

Beta 3 adrenergic receptor (β3-AR) is located in adipocytes. This receptor is involved in the epinephrine- and norepinephrine-induced activation of adenylate cyclase through the action of G proteins. Activation of β3AR in adipocytes has been shown as a regulatory factor for transformation of white fat cells to brown fat cells via beige/brite cells [Cypess et al., Cell Metab. 2015, 21(1): 33-38]. In the present invention, composition-7 dose dependently induces overexpression of β3AR in mouse adipocytes as depicted in Figure I. Thus, composition-7 has the potential to increase the lean body mass through the conversion of white fat cells into brown fat cells or browning of white fat.

The inventors of the present invention also evaluated the composition-7 comprising extracts selected from *Moringa oleifera*, *Murraya koenigii* and *Curcuma longa* for improving lean body mass in a clinical study. The body weights were measured for the subjects in the placebo and treatment groups at base line and on the final day. Similarly, the body fat compositions were measured using DEXA instrument at base line and on the final day. The lean body mass was calculated using the standard formula for the subjects both in placebo and treatment groups and the data is summarized in Table-7. Interestingly, the data showed that supplementation of subjects with said composition-7 increases the lean body mass (Figure IIA) and decreases the fat body mass (Figure IIB).

The forgoing thus demonstrates that the extracts or fractions derived from *Moringa oleifera*, *Murraya koenigii* and *Curcuma longa* and the synergistic compositions comprising the extracts derived *Moringa oleifera*, *Murraya koenigii* and *Curcuma longa* are potent natural supplements for a) treating the complications related to Advanced Glycation End (AGE) products by inhibiting excessive generation of AGE, b) conversion of white adipose tissue into brown adipose tissue or browning of fat and c) increasing the lean body mass by increase of UCP1 and increase of FGF21.

Therefore, one important embodiment of the present invention is to provide a synergistic composition comprising extracts or fractions or phytochemicals or mixtures thereof derived from *Moringa oleifera*, *Murraya koenigii* and *Curcuma longa* for increasing lean body mass and brown adipose tissue; for accelerating the conversion of the white adipose tissue (WAT) to brown adipose tissue (BAT).

In yet another embodiment the present invention discloses a synergistic composition comprising extracts or fractions or phytochemicals or mixtures thereof derived from *Moringa oleifera*, *Murraya koenigii* and *Curcuma longa* for increasing lean body mass and brown adipose tissue; for accelerating the conversion of the white adipose tissue (WAT) to brown adipose tissue (BAT), wherein the weight of *Moringa oleifera* derived component varies in the range of 10%-90%, the weight of *Murraya koenigii* derived component varies in the range of 10%-90% and the weight of *Curcuma longa* derived component varies in the range of 5%-30%.

In yet another embodiment the present invention discloses a synergistic composition comprising extracts or fractions or phytochemicals or mixtures thereof derived from *Moringa oleifera*, *Murraya koenigii* and *Curcuma longa* for increasing lean body mass and brown adipose tissue; for accelerating the conversion of the white adipose tissue (WAT) to brown adipose tissue (BAT), wherein the weight of *Moringa oleifera* derived component varies in the range of 30%-80%, the weight of *Murraya koenigii* derived component varies in the range of 10%-60% and the weight of *Curcuma longa* derived component varies in the range of 5%-20%.

In another embodiment, the present invention discloses a synergistic composition (Composition-1; C-1) containing 6 parts of *Moringa oleifera* 75% ethanol extract, 3 parts of *Murraya koenigii* 60% ethanol extract and 1 part of *Curcuma longa* extract standardized to 95% total curcuminoids for increasing lean body mass and brown adipose tissue; for accelerating the conversion of the white adipose tissue (WAT) to brown adipose tissue (BAT).

In another embodiment, the present invention discloses a synergistic composition (Composition-7; C-7) containing 6 parts of *Moringa oleifera* 90% ethanol extract, 3 parts of *Murraya koenigii* 60% ethanol extract and 1 part of *Curcuma longa* extract standardized to 95% total curcuminoids for increasing lean body mass and brown adipose tissue; for accelerating the conversion of the white adipose tissue (WAT) to brown adipose tissue (BAT).

In another embodiment, the present invention discloses a synergistic composition comprising extracts or fractions or phytochemicals or mixtures thereof derived from *Moringa oleifera*, *Murraya koenigii* and *Curcuma longa* and optionally containing at least one additional ingredient selected from pharmaceutically acceptable excipients, pharmaceutically acceptable diluents, and pharmaceutically acceptable carriers for increasing lean body mass and brown adipose tissue; for accelerating the conversion of the white adipose tissue (WAT) to brown adipose tissue (BAT).

In yet another embodiment the invention discloses a method of increasing lean body mass and brown adipose tissue and method of converting the white adipose tissue (WAT) to brown adipose tissue (WAT) in mammals wherein the method comprises supplementing mammals with an effective dose of a synergistic composition comprising the extracts or fractions or phytochemicals or mixtures thereof derived from *Moringa oleifera*, *Murraya koenigii* and *Curcuma longa* and optionally containing at least one additional ingredient selected from pharmaceutically, nutraceutically and dietically acceptable excipients, diluents, and carriers.

In another preferred embodiment, the present invention discloses a synergistic composition comprising extracts or fractions or phytochemicals or mixtures thereof derived from *Moringa oleifera*, *Murraya koenigii* and *Curcuma longa* for inhibiting excessive generation of advanced glycation end (AGE) products and for treating disease indications associated with increased levels of advanced glycation end (AGE) products.

In yet another embodiment the present invention discloses a synergistic composition comprising extracts or fractions or phytochemicals or mixtures thereof derived from *Moringa oleifera, Murraya koenigii* and *Curcuma longa* for inhibiting excessive generation of advanced glycation end (AGE) products and for treating disease indications associated with increased levels of advanced glycation end (AGE) products, wherein the weight of *Moringa oleifera* derived component varies in the range of 10%-90%, the weight of *Murraya koenigii* derived component varies in the range of 10%-90% and the weight of *Curcuma longa* derived component varies in the range of 5%-30%.

In yet another embodiment the present invention discloses a synergistic composition comprising extracts or fractions or phytochemicals or mixtures thereof derived from *Moringa oleifera, Murraya koenigii* and *Curcuma longa* for inhibiting excessive generation of advanced glycation end (AGE) products and for treating disease indications associated with increased levels of advanced glycation end (AGE) products, wherein the weight of *Moringa oleifera* derived component varies in the range of 30%-80%, the weight of *Murraya koenigii* derived component varies in the range of 10%-60% and the weight of *Curcuma longa* derived component varies in the range of 5%-20%.

In another embodiment, the present invention discloses a synergistic composition (Composition-1; C-1) containing 6 parts of *Moringa oleifera* 75% ethanol extract, 3 parts of *Murraya koenigii* 60% ethanol extract and 1 part of *Curcuma longa* extract standardized to 95% total curcuminoids for inhibiting excessive generation of advanced glycation end (AGE) products.

In another embodiment, the present invention discloses a synergistic composition (Composition-7; C-7) containing 6 parts of *Moringa oleifera* 90% ethanol extract, 3 parts of *Murraya koenigii* 60% ethanol extract and 1 part of *Curcuma longa* extract standardized to 95% total curcuminoids for inhibiting excessive generation of advanced glycation end (AGE) products.

In another embodiment, the present invention discloses a synergistic composition comprising extracts or fractions or phytochemicals or mixtures thereof derived from *Moringa oleifera, Murraya koenigii* and *Curcuma longa* and optionally containing at least one additional ingredient selected from pharmaceutically, nutraceutically and dietically acceptable excipients, diluents, and carriers for inhibiting excessive generation of advanced glycation end (AGE) products.

In yet another embodiment the invention discloses a method of inhibiting excessive generation of advanced glycation end (AGE) products and treating disease conditions related to advanced glycation end (AGE) products in mammals, wherein the method comprises supplementing mammals with an effective dose of a synergistic composition comprising extracts or fractions or phytochemicals or mixtures thereof derived from *Moringa oleifera, Murraya koenigii* and *Curcuma longa* and optionally containing at least one additional ingredient selected from pharmaceutically, nutraceutically and dietically acceptable excipient, diluent, and carrier.

In yet another embodiment the invention discloses a method of inhibiting excessive generation of advanced glycation end (AGE) products and treating the disease conditions associated with advanced glycation end (AGE) products in mammals by supplementing mammals with an effective dose of a synergistic composition comprising extracts or fractions or phytochemicals or mixtures thereof derived from *Moringa oleifera, Murraya koenigii* and *Curcuma longa* and optionally containing at least one additional ingredient selected from pharmaceutically, nutraceutically and dietically acceptable excipient, diluent, and carrier; wherein the disease conditions related to AGE's include but not limited to diabetes, retinopathy, nephropathy, neuropathy, cardiomyopathy, rheumatoid arthritis, osteoporosis, aging, cancer and progression of age-related neurodegenerative diseases like Alzheimer's disease.

In another embodiment, the present invention discloses a synergistic composition comprising extracts or fractions or phytochemicals or mixtures thereof derived from *Moringa oleifera, Murraya koenigii* and *Curcuma longa* and optionally containing at least one additional ingredient selected from pharmaceutically, nutraceutically and dietically acceptable excipient, diluent, and carrier for increasing lean body mass and brown adipose tissue; for accelerating the conversion of the white adipose tissue (WAT) to brown adipose tissue (WAT), inhibiting excessive generation of advanced glycation end (AGE) products and treating disease conditions associated with advanced glycation end (AGE) products in mammals; wherein the pharmaceutically acceptable excipient, diluent, and carrier include but not limited to glucose, fructose, sucrose, maltose, yellow dextrin, white dextrin, aerosil, microcrystalline cellulose, neusilin, calcium stearate, magnesium stearate, sorbitol, stevioside, corn syrup, lactose, citric acid, tartaric acid, malic acid, succinic acid, lactic acid, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, nicotinamide, pigments, flavors, preservatives, distilled water, saline, aqueous glucose solution, alcohol, propylene glycol and polyethylene glycol, various animal and vegetable oils, white soft paraffin, paraffin, flavorants, colorants and wax.

In another embodiment, the present invention discloses synergistic compositions comprising extracts or fractions or phytochemicals or mixtures thereof derived from *Moringa oleifera, Murraya koenigii* and *Curcuma longa* and optionally containing at least one additional ingredient selected from pharmaceutically, nutraceutically and dietically acceptable excipient, diluent, and carrier for increasing lean body mass and brown adipose tissue; for accelerating the conversion of the white adipose tissue (WAT) to brown adipose tissue (WAT), inhibiting excessive generation of advanced glycation end (AGE) products and treating disease conditions associated with advanced glycation end (AGE) products in mammals; wherein the solvents used for preparing the extracts, fractions and phytochemicals, include but not limited to C1-C5 alcohols, like ethanol, methanol; water and mixtures thereof, C1-C7 hydrocarbons such as hexane; esters like ethyl acetate and the like and mixtures thereof.

In another embodiment, the present invention discloses synergistic compositions comprising extracts or fractions or phytochemicals or mixtures thereof derived from *Moringa oleifera, Murraya koenigii* and *Curcuma longa* and optionally containing at least one additional ingredient selected from pharmaceutically, nutraceutically and dietically acceptable excipient, diluent, and carrier for increasing lean body mass and brown adipose tissue; for accelerating the conversion of the white adipose tissue (WAT) to brown adipose tissue (WAT), inhibiting excessive generation of advanced glycation end (AGE) products and treating disease conditions associated with advanced glycation end (AGE)

products in mammals; wherein the plant parts used for preparing the extracts, fractions and phytochemicals, include but not limited to leaves, stems, tender stem, aerial parts, fruit, fruit rind, seed, flower heads, root, bark, rhizome or whole plant or mixtures thereof.

In another embodiment, the present invention discloses a synergistic composition comprising extracts or fractions or phytochemicals or mixtures thereof derived from *Moringa oleifera*, *Murraya koenigii* and *Curcuma longa* and optionally containing at least one additional ingredient selected from pharmaceutically, nutraceutically and dietically acceptable excipient, diluent, and carrier for increasing lean body mass and brown adipose tissue; for accelerating the conversion of the white adipose tissue (WAT) to brown adipose tissue (WAT), inhibiting excessive generation of advanced glycation end (AGE) products and treating disease conditions associated with advanced glycation end (AGE) products in mammals; wherein composition(s) of the present invention may be formulated in solid form, liquid form, food product, dietary supplement or any suitable dosage forms such as tablet, a capsule or a soft chew, controlled release tablets, using controlled release polymer-based coatings by the techniques including nanotechnology, microencapsulation, colloidal carrier systems and other drug delivery systems.

In yet another embodiment the invention provides the use of these synergistic compositions comprising extracts or fractions or phytochemicals or mixtures thereof derived from *Moringa oleifera*, *Murraya koenigii* and *Curcuma longa* and optionally containing at least one additional ingredient selected from pharmaceutically, nutraceutically and dietically acceptable excipient, diluent, and carrier for inhibiting excessive generation of advanced glycation end (AGE) products and treating advanced glycation end (AGE) products related diseases in mammals.

In yet another embodiment the invention provides the use of these synergistic compositions comprising extracts or fractions or phytochemicals or mixtures thereof derived from *Moringa oleifera*, *Murraya koenigii* and *Curcuma longa* and optionally containing at least one additional ingredient selected from pharmaceutically, nutraceutically and dietically acceptable excipient, diluent, and carrier for increasing lean body mass and brown adipose tissue and converting the white adipose tissue (WAT) to brown adipose tissue (WAT) in mammals.

Those of ordinary skilled in the art will appreciate that changes could be made to the embodiments described above without departing from the broad inventive concept thereof. It is understood, therefore, that this invention is not limited to the particular embodiments or examples disclosed herein, but is intended to cover modifications within the objectives and scope of the present invention as defined in the specification. The presented examples illustrate the invention, but they should not be considered to limit the scope of the invention in any way.

Example 1: Preparation of *Moringa oleifera* Ethanol Extract

*Moringa oleifera* leaf (100 g) was pulverized and extracted with ethanol (700 mL) at rt for 1 h. The extract was filtered and the spent raw material was re-extracted twice with ethanol (2×500 mL) under similar conditions. The combined extract was filtered and concentrated under vacuum to obtain a residue of ethanol extract as dry powder (M.O-1; 8.7 g).

Example 2: Preparation of *Moringa oleifera* Aqueous Ethanol Extracts

*Moringa oleifera* leaf (100 g) was pulverized and extracted with 90% aqueous ethanol (700 mL) at 65-70° C. for 1 h. The extract was filtered and the spent raw material was re-extracted twice with 90% aqueous ethanol (2×500 mL) under similar conditions. The combined extract was filtered and concentrated under vacuum to obtain 90% aqueous alcohol extract as dry powder (M.O-2; 20 g). The 75% aqueous ethanol extract (M.O-3; 22 g) and 50% aqueous ethanol extract (M.O-4; 22 g) were obtained by adopting similar procedure using 75% aqueous ethanol and 50% aqueous ethanol as extraction solvents respectively.

Example 3: Preparation of *Moringa oleifera* Methanol and Water Extracts

*Moringa oleifera* leaf (100 g) was pulverized and extracted with methanol (700 mL) at rt for 1 h. The extract was filtered and the spent raw material was re-extracted twice with methanol (2×500 mL) under similar conditions. The combined extract was filtered and concentrated under vacuum to obtain a residue of methanol extract as dry powder (M.O-5; 20 g).

The water extract (M.O-6; 26 g) was obtained by adopting similar procedure using water as extraction solvent.

Standardization: The above *Moringa oleifera* extracts were standardized to quercetin-3-O-glycoside by analytical HPLC method and the results were summarized in Table 1.

TABLE 1

Details of *Moringa oleifera* extracts

| S. No. | Extract code | Solvent for extraction | Weight of the product | Quercetin-3-O-glycoside (HPLC) |
|---|---|---|---|---|
| 1 | M.O-1 | Ethanol | 8.7 g | 1.56% |
| 2 | M.O-2 | 90% aqueous ethanol | 20 g | 1.34% |
| 3 | M.O-3 | 75% aqueous ethanol | 22 g | 1.13% |
| 4 | M.O-4 | 50% aqueous ethanol | 22 g | 0.55% |
| 5 | M.O-5 | Methanol | 20 g | 1.90% |
| 6 | M.O-6 | Water | 26 g | 0.15% |

Example 4: Preparation of *Murraya koenigii* Ethanol Extract

*Murraya koenigii* leaf (100 g) was pulverized and extracted with ethanol (700 mL) at rt for 1 h. The extract was filtered and the spent raw material was re-extracted twice with ethanol (2×500 mL) under similar conditions. The combined extract was filtered and concentrated under vacuum to obtain a residue of ethanol extract as dry powder (M.K-1; 4.6 g).

Example 5: Preparation of *Murraya koenigii* Aqueous Ethanol Extracts

*Murraya koenigii* leaf (100 g) was pulverized and extracted with aqueous 60% ethanol (700 mL) at 65-70° C. for 1 h. The extract was filtered and the spent raw material was re-extracted twice with aqueous 60% ethanol (2×500 mL) under similar conditions. The combined extract was filtered and concentrated under vacuum to obtain a residue of ethanol extract as dry powder (M.K-2; 20 g). The aqueous 80% ethanol extract (M.K-3; 15 g) was obtained by adopting similar procedure using aqueous 80% ethanol as extraction solvent.

Example 6: Preparation of *Murraya koenigii* Aqueous 60% Methanol Extract

*Murraya koenigii* leaf (100 g) was pulverized and the powder was charged into a lab extractor and extracted with aqueous 60% methanol (700 mL) at 65-70° C. for 1 h. The extract was filtered and the spent raw material was re-extracted twice with aqueous 60% methanol (2×500 mL) under similar conditions. The combined extract was filtered and concentrated under vacuum to obtain a residue of aqueous 60% methanol extract as dry powder (M.K-4; 19 g).

Example 7: Preparation of *Murraya koenigii* Water Extract

*Murraya koenigii* leaf (100 g) was pulverized and extracted with water (700 mL) at rt for 1 h. The extract was filtered and the spent raw material was re-extracted twice with water (2×500 mL) under similar conditions. The combined extract was filtered and concentrated under vacuum to obtain water extract as dry powder (M.K-5; 16 g).

Standardization:

The above *Murraya koenigii* leaf extracts were standardized to mahanine by analytical HPLC method and the results were summarized in Table 2.

TABLE 2

Details of *Murraya koenigii* extracts

| S. No. | Extract code | Solvent for extraction | Weight of the product | Mahanine (HPLC) |
|---|---|---|---|---|
| 1 | M.K-1 | Ethanol | 9.0 g | 5.05% |
| 2 | M.K-2 | 60% aqueous ethanol | 20 g | 1.76% |
| 3 | M.K-3 | 80% aqueous ethanol | 15 g | 3.3% |
| 4 | M.K-4 | 60% aqueous methanol | 19 g | 1.80% |
| 5 | M.K-5 | Water | 16 g | 0.05% |

Example 8: *Curcuma longa* Extract Standardized to 95% Total Curcuminoids (C.L-1)

*Curcuma longa* extract (C.L-1) standardized to 95% total curcuminoids is widely available in the market and was procured from commercial source. The commercial material was tested against the in house curcumin markers for checking compliance to the in-house specification.

Example 9: Preparation of *Curcuma longa* Extracts

*Curcuma longa* rhizomes (500 g) were pulverized and extracted with 90% aqueous ethanol (700 mL) at 70-75° C. for 1 h. The extract was filtered and the spent raw material was re-extracted twice with 90% aqueous ethanol (2×500 mL) under similar conditions. The combined extract was filtered and concentrated under vacuum to obtain a residue of 90% ethanol extract as yellow color thick paste (C.L-2; 50 g). HPLC: Total curcuminoids: 24.8%.

The above C.L-2 sample (50 g) was dissolved in aqueous 80% ethanol (30 mL) under stirring at 60-65° C. for 0.5 h. The solution was settled for 16 h and the precipitated solid was filtered, washed with aqueous 50% ethanol and dried under reduced pressure to give the product as yellow color powder (C.L-3; 15 g). HPLC: Total curcuminoids: 40.0%.

Example 10: Preparation of Compositions Containing *Moringa oleifera* Extract, *Murraya koenigii* Extract and *Curcuma longa* Extract Composition-1 (C-1): The composition-1 was prepared by combining 75% ethanol extract of *Moringa oleifera* (M.O-3), 60% ethanol extract of *Murraya koenigii* (M.K-2) and *Curcuma longa* extract standardized to 95% total curcuminoids (C.L-1) in the ratio of 6:3:1.

Composition-2 (C-2): The composition-2 was prepared by combining 75% ethanol extract of *Moringa oleifera* (M.O-3), 60% ethanol extract of *Murraya koenigii* (M.K-2) and *Curcuma longa* extract standardized to 95% total curcuminoids (C.L-1) in the ratio of 8:1:1.

Composition-3 (C-3): The composition-3 was prepared by combining 75% ethanol extract of *Moringa oleifera* (M.O-3), 60% ethanol extract of *Murraya koenigii* (M.K-2) and *Curcuma longa* extract standardized to 95% total curcuminoids (C.L-1) in the ratio of 4:5:1.

Composition-4 (C-4): The composition-4 was prepared by combining 75% ethanol extract of *Moringa oleifera* (M.O-3), 60% ethanol extract of *Murraya koenigii* (M.K-2) and *Curcuma longa* extract standardized to 95% total curcuminoids (C.L-1) in the ratio of 2:2:1.

Composition-5 (C-5): The composition-5 was prepared by combining 75% ethanol extract of *Moringa oleifera* (M.O-3), 60% ethanol extract of *Murraya koenigii* (M.K-2) and *Curcuma longa* extract standardized to 95% total curcuminoids (C.L-1) in the ratio of 3:6:1.

Composition-6 (C-6): The composition-6 was prepared by combining 75% ethanol extract of *Moringa oleifera* (M.O-3), 60% ethanol extract of *Murraya koenigii* (M.K-2) and *Curcuma longa* extract standardized to 95% total curcuminoids (C.L-1) in the ratio of 6:3.5:0.5.

Composition-7 (C-7): The composition-7 was prepared by combining 90% ethanol extract of *Moringa oleifera* (M.O-2). 60% ethanol extract of *Murraya koenigii* (M.K-2) and *Curcuma longa* extract standardized to 95% total curcuminoids (C.L-1) in the ratio of 6:3:1.

Composition-8 (C-8): The composition-8 was prepared by combining 50% ethanol extract of *Moringa oleifera* (M.O-4), 60% ethanol extract of *Murraya koenigii* (M.K-2) and *Curcuma longa* extract standardized to 95% total curcuminoids (C.L-1) in the ratio of 6:3:1.

Composition-9 (C-9): The composition-9 was prepared by combining methanol extract of *Moringa oleifera* (M.O-5), 60% ethanol extract of *Murraya koenigii* (M.K-2) and *Curcuma longa* extract standardized to 95% total curcuminoids (C.L-1) in the ratio of 6:3:1.

Composition-10 (C-10): The composition-10 was prepared by combining water extract of *Moringa oleifera* (M.O-6), 60% ethanol extract of *Murraya koenigii* (M.K-2) and *Curcuma longa* extract standardized to 95% total curcuminoids (C.L-1) in the ratio of 6:3:1.

Composition-11 (C-11): The composition-11 was prepared by combining 75% ethanol extract of *Moringa oleifera* (M.O-3), ethanol extract of *Murraya koenigii* (M.K-1) and *Curcuma longa* extract standardized to 95% total curcuminoids (C.L-1) in the ratio of 6:3:1.

Composition-12 (C-12): The composition-12 was prepared by combining 75% ethanol extract of *Moringa oleifera* (M.O-3), 80% ethanol extract of *Murraya koenigii* (M.K-3) and *Curcuma longa* extract standardized to 95% total curcuminoids (C.L-1) in the ratio of 6:3:1.

Composition-13 (C-13): The composition-13 was prepared by combining 75% ethanol extract of *Moringa oleifera* (M.O-3), 60% methanol extract of *Murraya koenigii* (M.K-4) and *Curcuma longa* extract standardized to 95% total curcuminoids (C.L-1) in the ratio of 6:3:1.

Composition-14 (C-14): The composition-14 was prepared by combining 75% ethanol extract of *Moringa oleifera* (M.O-3), water extract of *Murraya koenigii* (M.K-5) and *Curcuma longa* extract standardized to 95% total curcuminoids (C.L-1) in the ratio of 6:3:1.

Composition-15 (C-15): The composition-15 was prepared by combining 75% ethanol extract of *Moringa oleifera* (M.O-3), 60% ethanol extract of *Murraya koenigii* (M.K-2) and *Curcuma longa* extract standardized to 40% total curcuminoids (C.L-3) in the ratio of 6:3:1.

Composition-16 (C-16): The composition-16 was prepared by combining 75% ethanol extract of *Moringa oleifera* (M.O-3), 60% ethanol extract of *Murraya koenigii* (M.K-2) and *Curcuma longa* extract standardized to 40% total curcuminoids (C.L-2) in the ratio of 6:3:1.

Example 11: Uncoupling Protein 1 (UCP1) Assay

Mouse 3T3-L1 pre-adipocytes (150000 cells/well in 3 mL) were seeded in a 6-well cell culture plate and maintained in DMEM medium containing 10% FBS and 4.5 g/L glucose at 37° C. in a humidified atmosphere of 5% $CO_2$. After the cells were confluent (~2 days), differentiation was initiated using differentiation medium (DM) containing 0.5 mM IBMX, 1 µM dexamethasone, and 500 nM insulin in DMEM with 10% FBS for 48 hours. The cell culture medium was changed to post-DM containing 100 nM insulin in DMEM with 10% FBS and post-DM was freshly replaced every 48 hours until day 6. On day 7, medium was aspirated from the wells and they were washed twice with DMEM medium containing 1% FBS. Cells were treated with different concentrations of test samples (50 µL) in DMEM medium containing 1% FBS (1 mL total volume) and incubated for another 48 hours at 37° C. in a $CO_2$ incubator.

Western blot: After the incubation, cell culture plates were placed on ice tray and washed twice with 1×PBS. Eighty microliters of lysis buffer (10 mM Tris-HCl pH 7.4, 150 mM NaCl, 1 mM EDTA, 1 mM PMSF, 10 µg/mL Aprotinin, 10 µg/mL Leupeptin, 1% Triton X-100, 1 mM NaF, 1 mM $Na_3VO_4$, 0.5% Sodium deoxycholate, and 1 µM Pepstatin) was added to each well and the cell lysates were collected in respective microfuge tubes. The microfuge tubes were sonicated for 1 min. and cellular protein was collected after centrifugation at 21952×g. Protein was quantified using Pierce BCA protein assay kit (Thermo Scientific Cat #23225). SDS-PAGE was performed for the protein samples and resolved proteins were transferred onto nitrocellulose membrane using wet blotting method. Briefly, 10 µg of protein was loaded onto acrylamide gel (10% resolving) and ran at 100V for approximately 1 hr 40 min. At the end of the run, proteins were transferred to the nitrocellulose membrane by placing transfer system at 4° C. chamber (100V for 2 hrs). After the transfer, UCP-1 was probed using anti-UCP-1 antibody (Thermo Scientific Cat #PA1-24894; 1:1000 dilution) incubating at 4° C. for 18 hrs. β-Actin was probed using anti-β-actin antibody (Sigma Cat #A4700-100 uL; 1:10000 dilution) incubating at room temperature for 2 hrs. Peroxidase affinipure mouse anti-goat secondary antibody (Jackson Immuno Research Cat #205-035-108; 1:10000 dilution) was added and incubated for 30 mins. at room temperature. Finally, the blots were developed using a chemiluminiscent substrate (Thermo Scientific Cat #34080) and images were captured using Bio-Rad Molecular imager (Model: ChemiDOC XRS+). The intensities of the protein bands were calculated using Carestream MI software and normalized using β-Actin. Relative index of UCP1 expression was obtained by calculating the ratio between the band intensities for the cells treated with test compounds or control and β-Actin. The data is summarized in Table 3.

TABLE 3

UCP1 activity of the compositions

| Composition | Dose µg/mL | Relative index of UCP1 expression against β-Actin |
|---|---|---|
| Control |   | 0.600 |
| C-1 | 5 | 0.928 |
| C-2 | 5 | 0.890 |
| C-3 | 5 | 0.920 |
| C-4 | 5 | 0.975 |
| C-5 | 5 | 0.912 |
| C-6 | 5 | 0.934 |
| C-7 | 5 | 0.886 |
| C-8 | 5 | 0.906 |
| C-9 | 5 | 0.940 |
| C-10 | 5 | 0.860 |
| C-11 | 5 | 0.920 |
| C-12 | 5 | 0.940 |
| C-13 | 5 | 0.956 |
| C-14 | 5 | 0.818 |
| C-15 | 5 | 0.945 |
| C-16 | 5 | 0.915 |

Example 12: Fibroblast Growth Factor 21 (FGF21) Assay

Mouse 3T3-L1 pre-adipocytes (150000 cells/well in 3 mL) were seeded in a 6-well cell culture plate and maintained in DMEM medium containing 10% FBS and 4.5 g/L glucose at 37° C. in a humidified atmosphere of 5% $CO_2$. After the cells were confluent (~2 days), differentiation was initiated using differentiation medium (DM) containing 0.5 mM IBMX, 1 µM dexamethasone, and 500 nM insulin in DMEM with 10% FBS for 48 hours. The cell culture medium was changed to post-DM containing 100 nM insulin in DMEM with 10% FBS and post-DM was freshly replaced every 48 hours until day 6. On day 7, medium was aspirated from the wells and they were washed twice with DMEM medium containing 1% FBS. Cells were treated with different concentrations of test samples (50 µL) in DMEM medium containing 1% FBS (1 mL total volume) and incubated for another 48 hours at 37° C. in a $CO_2$ incubator. After incubation, 50 µL of cell-free supernatants were collected from the wells and processed for FGF21 analysis by ELISA. FGF21 ELISA (R&D Systems Cat #DY2539) was performed according to the manufacturer's protocol. Percent increase in FGF21 was calculated using the formula below:

$$\% \text{ Increase of } FGF21 = \frac{FGF21 \text{ Concn. in Treatment} - FGF21 \text{ Concn. in Vehicle Control}}{FGF21 \text{ Concn. in Vehicle Control}}$$

The FGF21 increasing activity of the individual ingredients and compositions are summarized in Table 4

TABLE 4

FGF21 activity of the compositions

| Comp # | Dose μg/mL | % increase | Dose μg/mL | % increase | Dose μg/mL | % increase | Ratio | Comp dose μg/mL | % increase of FGF21 Additive (calculated) | Observed |
|---|---|---|---|---|---|---|---|---|---|---|
| | M.O-3 | | M.K-2 | | C.L-1 | | | | | |
| C-1 | 3.0 | 22.71 | 1.5 | 0.73 | 0.5 | 3.03 | 6:3:1 | 5 | 26.47 | 34.62 |
| C-2 | 4.0 | 23.26 | 0.5 | 0.32 | 0.5 | 3.03 | 8:1:1 | 5 | 26.61 | 30.12 |
| C-3 | 2.0 | 15.14 | 2.5 | 1.5 | 0.5 | 3.03 | 4:5:1 | 5 | 19.67 | 25.24 |
| C-4 | 2.0 | 15.14 | 2.0 | 1.23 | 1.0 | 4.65 | 4:4:2 | 5 | 21.02 | 26.32 |
| C-5 | 1.5 | 11.35 | 3.00 | 2.05 | 0.5 | 3.03 | 3:6:1 | 5 | 16.43 | 31.42 |
| C-6 | 3.0 | 22.71 | 1.75 | 0.96 | 0.25 | 1.52 | 6:3.5:0.5 | 5 | 25.19 | 31.26 |
| | M.O-2 | | M.K-2 | | CL-1 | | | | | |
| C-7 | 3.0 | 23.45 | 1.5 | 0.73 | 0.5 | 3.03 | 6:3:1 | 5 | 27.21 | 35.23 |
| | M.O-4 | | M.K-2 | | CL-1 | | | | | |
| C-8 | 3.0 | 15.21 | 1.5 | 0.73 | 0.5 | 3.03 | 6:3:1 | 5 | 18.97 | 22.54 |
| | M.O-5 | | M.K-2 | | CL-1 | | | | | |
| C-9 | 3.0 | 21.26 | 1.5 | 0.73 | 0.5 | 3.03 | 6:3:1 | 5 | 25.02 | 29.15 |
| | M.O-6 | | M.K-2 | | CL-1 | | | | | |
| C-10 | 3.0 | 8.65 | 1.5 | 0.73 | 0.5 | 3.03 | 6:3:1 | 5 | 12.41 | 15.23 |
| | M.O-3 | | M.K-1 | | CL-1 | | | | | |
| C-11 | 3.0 | 22.71 | 1.5 | 1.12 | 0.5 | 3.03 | 6:3:1 | 5 | 26.86 | 28.32 |
| | M.O-3 | | M.K-3 | | CL-1 | | | | | |
| C-12 | 3.0 | 22.71 | 1.5 | 0.86 | 0.5 | 0.61 | 6:3:1 | 5 | 24.18 | 27.54 |
| | M.O-3 | | M.K-4 | | CL-1 | | | | | |
| C-13 | 3.0 | 22.71 | 1.5 | 0.81 | 0.5 | 3.03 | 6:3:1 | 5 | 26.55 | 28.12 |
| | M.O-3 | | M.K-5 | | CL-1 | | | | | |
| C-14 | 3.0 | 22.71 | 1.5 | 0.26 | 0.5 | 3.03 | 6:3:1 | 5 | 26.00 | 30.49 |
| | M.O-3 | | M.K-2 | | C.L-3 | | | | | |
| C-15 | 3.0 | 19.42 | 1.5 | 0.73 | 0.5 | 1.7 | 6:3:1 | 5 | 21.85 | 23.65 |
| | M.O-3 | | M.K-2 | | C.L-2 | | | | | |
| C-16 | 3.0 | 21.34 | 1.5 | 0.73 | 0.5 | 1.23 | 6:3:1 | 5 | 23.3 | 24.67 |

Example 13: Advanced Glycation End Products (AGE) Assay

AGE formation assay was performed according to the method described earlier with minor modifications (Tupe et. al., 2015). Briefly, Compositions or their individual ingredients were reacted in a reaction mixture comprising 0.25 mL of 10 mg/mL bovine serum albumin (BSA) and 0.25 mL of 250 mM fructose and 0.5 mL of 1× Dulbecco's potassium phosphate buffer saline [1×DPBS, 200 μM, pH 7.4] containing 0.02% sodium azide. In parallel, the reaction mixture devoid of the test samples or fructose is considered as AGE induction or the negative control, respectively. In every reaction, the total reaction volume was 1.0 mL. The complete reaction mixtures were incubated in dark at 37° C. for 7 days in sealed tubes under sterile condition. In all reactions, DMSO concentration was maintained at 0.05%. After incubation period, the unbound fructose was removed by dialysis against 1×DPBS and fluorescence intensities of the dialysates were measured at Ex. 370 nm/Em440 nm in a multimode plate reader (Perkin-Elmer Enspire 2300, Waltham, MA). The relative fluorescence unit (RFU) value obtained in the negative control was used to normalize the data from the test samples and induction. Inhibition of AGE formation was calculated by the following formula. The results are summarized in Table 5.

$$\% \text{ inhibition of AGE formation} = \frac{\text{Normalized } RFU \text{ In induction} - \text{Normalized } RFU \text{ in Test}}{\text{Normalized in Induction}} \times 100$$

Reference: Tupe R S, Sankhe N M, Shaikh S A, Kemse N G, Khaire A A, Phatak D V, and Parikh J U. Nutraceutical properties of dietay plants extracts: prevention of diabetic nephropathy through inhibition of glycation and toxicity to erythrocytes and HEK293 cells. Phar. Biol. 2015; 53: 40-50.

TABLE 5

AGE inhibition activity of the compositions

| Comp # | Dose μg/mL | % inhibition | Dose μg/mL | % inhibition | Dose μg/mL | % inhibition | Ratio | Comp dose μg/mL | % inhibition of AGE Additive (calculated) | Observed |
|---|---|---|---|---|---|---|---|---|---|---|
| | M.O-3 | | M.K-2 | | CL-1 | | | | | |
| C-1 | 0.6 | 4.26 | 0.3 | 8.70 | 0.1 | 5.47 | 6:3:1 | 1 | 18.43 | 50.49 |
| C-2 | 0.8 | 4.01 | 0.1 | 2.31 | 0.1 | 5.47 | 8:1:1 | 1 | 11.79 | 20.38 |
| C-3 | 4.0 | 7.10 | 5.00 | 32.55 | 1.00 | 7.23 | 4:5:1 | 10 | 46.88 | 56.87 |
| C-4 | 0.4 | 2.49 | 0.4 | 8.92 | 0.2 | 6.54 | 4:4:2 | 1 | 17.95 | 21.67 |
| C-5 | 0.3 | 2.37 | 0.6 | 9.08 | 0.1 | 5.47 | 3:6:1 | 1 | 16.92 | 22.36 |
| C-6 | 0.6 | 4.26 | 0.35 | 10.15 | 0.05 | 2.02 | 6:3.5:0.5 | 1 | 16.43 | 76.93 |

TABLE 5-continued

AGE inhibition activity of the compositions

| Comp # | Dose µg/mL | % inhibition | Dose µg/mL | % inhibition | Dose µg/mL | % inhibition | Ratio | Comp dose µg/mL | % inhibition of AGE Additive (calculated) | Observed |
|---|---|---|---|---|---|---|---|---|---|---|
| | M.O-2 | | M.K-2 | | CL-1 | | | | | |
| C-7 | 0.6 | 17.32 | 0.3 | 8.70 | 0.1 | 5.47 | 6:3:1 | 1 | 31.49 | 72.70 |
| | M.O-4 | | M.K-2 | | CL-1 | | | | | |
| C-8 | 0.6 | 3.61 | 0.3 | 8.70 | 0.1 | 5.47 | 6:3:1 | 1 | 17.78 | 23.79 |
| | M.O-5 | | M.K-2 | | CL-1 | | | | | |
| C-9 | 6.0 | 8.78 | 3.00 | 19.53 | 1.0 | 7.23 | 6:3:1 | 10 | 35.54 | 38.86 |
| | M.O-6 | | M.K-2 | | CL-1 | | | | | |
| C-10 | 0.6 | 12.34 | 0.3 | 8.70 | 0.1 | 4.16 | 6:3:1 | 1 | 25.2 | 69.51 |
| | M.O-3 | | M.K-1 | | CL-1 | | | | | |
| C-11 | 0.6 | 4.26 | 0.3 | 9.06 | 0.1 | 5.47 | 6:3:1 | 1 | 18.79 | 24.09 |
| | M.O-3 | | M.K-3 | | CL-1 | | | | | |
| C-12 | 0.6 | 4.26 | 0.3 | 13.54 | 0.1 | 4.16 | 6:3:1 | 1 | 21.96 | 24.28 |
| | M.O-3 | | M.K-4 | | CL-1 | | | | | |
| C-13 | 0.6 | 4.26 | 0.3 | 12.68 | 0.1 | 5.47 | 6:3:1 | 1 | 22.41 | 25.37 |
| | M.O-3 | | M.K-5 | | CL-1 | | | | | |
| C-14 | 0.6 | 4.26 | 0.3 | 7.28 | 0.1 | 5.47 | 6:3:1 | 1 | 17.01 | 22.07 |
| | M.O-3 | | M.K-2 | | C.L-3 | | | | | |
| C-15 | 0.6 | 4.26 | 0.3 | 8.70 | 0.1 | 3.10 | 6:3:1 | 1 | 16.06 | 21.55 |
| | M.O-3 | | M.K-2 | | C.L-2 | | | | | |
| C-16 | 0.6 | 4.26 | 0.3 | 8.70 | 0.1 | 2.12 | 6:3:1 | 5 | 15.08 | 54.43 |

Example 14: Proteome Profding Assay

Proteome profiling assay revealed modulations of some key markers of Advanced Glycation End products (AGE). The assay was performed on the pooled serum samples obtained from a randomized double blind clinical study conducted on healthy overweight subjects. One hundred and forty subjects (Body mass index 27 to 29.9 kg/m2, 29.3% male; ages 21-50 years) were randomized into Placebo (n=70) and Composition-7 (n=70) groups. The subjects received either 900 mg/day of Composition-7 in two divided doses or two identical placebo capsules for 16 weeks. At the end of the trial period, the collected serum samples were pooled group wise. The pooled serum samples were analyzed for modulation in expressions of different biomarkers using a commercial Proteome profiler kit (Adipokine Array kit, R&D systems, Minneapolis, MN). The assay procedure was essentially the same as the instructions provided by the kit manufacturer. Briefly, the individual nitrocellulose membrane each containing different capture antibodies printed in duplicate was reacted with the pooled serum samples of either placebo or Composition-7. The immunoreactive spots on the membranes were developed using Chemi Reagent Mix supplied in the kit. The images of chemiluminescent spots on the membranes were captured by a Molecular imager (ChemiDoc XRS+, BioRad, Hercules, CA). Densitometric analyses of immunoreactions on captured images were performed by a Molecular Imaging Software, Version 5.0 (Carestream Molecular Imaging, New Haven, CT). The results of the modulation of markers related to AGE products by Composition-7 in comparison to placebo are summarized in Table 6.

TABLE 6

Down-regulation of Advanced Glycation end products (AGE) related markers in Composition-7 supplemented Human serum samples

| Biomarkers | Average density (Arbitrary units) | | Relative Expression in Composition-7 (wrt. Placebo) |
|---|---|---|---|
| | Placebo | Composition 7 | |
| EN-RAGE | 145667 | 95959 | 0.658 |
| IL-6 | 257890.5 | 33392 | 0.129 |
| CXCL8/IL-8 | 549686 | 439219 | 0.799 |

Example 15: Composition-7 Induces Overexpression of Beta 3 Adrenergic Receptor (β3AR) in 3T3-L1 Adipocytes Cell culture and treatment: Mouse pre-adipocyte 3T3-L1 cells were maintained in Dulbecco's Modified Eagles Medium (DMEM) supplemented with 2 mM glutamine, 4.5 g/L glucose and 10% fetal bovine serum. Equal number of cells was plated in each well of 24-well culture plates. Cells were pre-treated with 10 and 25 µg/ml of Composition-7 for 2h and followed by addition of differentiation medium containing 500 nM insulin, 1.0 µM dexamethasone, and 0.5 mM isobutylmethylxanthine (IBMX) for 48h. Thereafter, cells were further incubated with post differentiation medium (DMEM containing 100 nM insulin) in presence or absence of Composition-7. Vehicle control cells were treated with 0.2% DMSO. Finally, the cells were harvested, washed with chilled phosphate buffered saline and lysed with the lysis buffer. The protein extracts were clarified at 14,000 g for 20 min. Protein content was measured in Bradford method by using Coomassie blue dye and cell lysates were stored in aliquots at −80° C. until further use.

The modulation of β3 adrenergic receptor (β3AR) protein expression in Composition-7 treated cells was evaluated using immuno blot assay as described below.

Western blot Assay: Briefly, equal amount of cell lysates proteins was resolved in 7.5% SDS-PAGE; thereafter, the proteins were transferred to nitrocellulose membrane. After blocking the non-specific sites, the membrane was incubated with β3AR antibody (United States Biological, Salem, MA). Finally, the specific immuno-reactive bands were developed with SuperSignal West-Pico chemiluminescent substrate (Thermo Fisher Scientific, Waltham, MA), and the immunoblot images were recorded in a Kodak Image Station (Kodak, USA). The blotted membrane was stripped and re-probed with 0-actin antibody (Sigma Chemical Co, St. Luis, MO). The band intensities were calculated densitometrically and normalized with expression of actin. The composition-7 dose dependently over expressed the β3AR as depicted in Figure I.

Example 16: Mean Change in Body Composition

The randomized, double blind, Placebo controlled clinical study was performed on human subjects to evaluate the efficacy of Composition-7. One hundred forty eligible subjects were randomized into either Treatment group or Placebo group. The subjects in the treatment group were supplemented with 900 mg (450 mg capsules, twice daily) of Composition-7 or placebo group subjects were given similar looking placebo for 112 days. Sixty six subjects in treatment group and sixty six subjects in placebo group completed the study. The Fat Mass (FM) was measured on base line and on the day of final visit using DEXA instrument along with body total weight (BW). The lean body mass (LBM) for all the subjects was calculated based on the formula LBM=BW-FM and the data is summarized in the following Table 7. At the end of the trial period, lean body mass was significantly (p=0.0061) increased in subjects in the treatment group supplemented with Composition-7 by 0.90±0.464 kg; whereas, in placebo group, it was decreased by 0.91±0.453 kg from the baseline. The mean change in lean body mass (A) and mean change in fat body mass (B) are depicted in Figure H.

TABLE 7

Mean change in Body composition

| Variable | Treatment (n = 65) | Placebo (n = 64) | p Value(a) |
|---|---|---|---|
| Total lean body mass (Kg) | | | |
| Baseline (Mean ± S.E.) | 41.26 ± 0.964 | 41.37 ± 1.017 | 0.9382 |
| Final Visit (Mean ± S.E.) | 42.16 ± 1.081 | 40.46 ± 0.932 | 0.2363 |
| Mean Difference (Mean ± S.E.) | 0.90 ± 0.464 | −0.91 ± 0.453 | 0.0061* |
| p value(b) | 0.0570 | 0.0490 | |
| Total lean fat mass (Kg) | | | |
| Baseline (Mean ± S.E.) | 33.17 ± 1.187 | 30.60 ± 0.987 | 0.0986 |
| Final Visit (Mean ± S.E.) | 32.06 ± 1.163 | 31.20 ± 1.025 | 0.5827 |
| Mean Difference (Mean ± S.E.) | −1.11 ± 0.876 | 0.61 ± 0.632 | 0.1151* |
| p value(b) | 0.2098 | 0.3395 | |

Note:
p Value (a): Unpaired t-test between the groups. p Value(b): Paired t-test between baselines with respective visits. And in column p Value (a), * represents the p value for mean difference with respective to visit.

We claim:

1. A method of inhibiting excessive generation of advanced glycation end (AGE) products in a mammal in need thereof, wherein the method comprises administering to the mammal a herbal composition comprising:
   from 10% to 90% by weight of an extract of Moringa oleifera,
   from 10% to 90% by weight of an extract of Murraya koenigii, and
   from 5% to 30% by weight of an extract of Curcuma longa;
   wherein the extract of Curcuma longa is prepared by a process consisting of only one or more extraction steps of Curcuma longa rhizome with aqueous ethanol.

2. The method of claim 1, wherein the herbal composition further comprises:
   a pharmaceutically, nutraceutically or dietically acceptable excipient,
   a pharmaceutically, nutraceutically or dietically acceptable carrier,
   a pharmaceutically, nutraceutically or dietically acceptable diluent, or
   a mixture thereof.

3. The method of claim 1, wherein the herbal composition further comprises at least one pharmaceutically, nutraceutically or dietically acceptable excipient, carrier, or diluent, wherein the excipient, carrier, or diluent is selected from the group consisting of glucose, fructose, sucrose, maltose, sucralose, Aceldama K, yellow dextrin, white dextrin, aerosil, microcrystalline cellulose, neusilin, calcium stearate, magnesium stearate, sorbitol, stevioside, monoammonium glycyrrhizinate, sodium alginate, corn syrup, lactose, citric acid, tartaric acid, malic acid, succinic acid, lactic acid, L-ascorbic acid, dl-alpha-tocopherol, glycerin, propylene glycol, a glycerol fatty ester, a poly(glycerol fatty ester), a sucrose fatty ester, a sorbitan fatty ester, a propylene glycol fatty ester, acacia, carrageenan, casein, gelatin, pectin, agar, vitamin B group, nicotinamide, calcium pantothenate, an amino acid, a protein, a calcium salt, a pigment, a preservative, distilled water, a saline solution, an aqueous glucose solution, alcohol, propylene glycol, polyethylene glycol, an animal oil, vegetable oil, white soft paraffin, paraffin, a flavorant, a colorant, a wax, or and mixtures thereof.

4. The method of claim 1, wherein the extracts of Moringa oleifera, Murraya koenigii, and Curcuma longa are each obtained by extraction of at least one plant part selected from the group consisting of leaves, stems, tender stem, aerial parts, a fruit, a fruit rind, a seed, a flower head, a root, bark, a rhizome, a whole plant, and mixtures thereof.

5. The method of claim 1, wherein the extracts of Moringa oleifera, Murraya koenigii, and Curcuma longa are each obtained by extraction with a solvent selected from the group consisting of C1-C5 alcohols, ketones, water, chlorinated solvents, C1-C7 hydrocarbons, and mixtures thereof.

6. The method of claim 5, wherein the extracts of Moringa oleifera, Murraya koenigii, and Curcuma longa are each obtained by extraction with a solvent selected from the group consisting of C1-C5 alcohols, water, and mixtures thereof.

7. The method of claim 1, wherein the extracts of Moringa oleifera, Murraya koenigii, and Curcuma longa are each obtained by extraction with a solvent selected from the group consisting of ethanol, methanol, n-propanol, isopropyl alcohol, acetone, methyl isobutyl ketone, water, methylene dichloride, chloroform, hexane, ethyl acetate, and mixtures thereof.

8. The method of claim 1, wherein the extract of *Moringa oleifera* and the extract of *Murraya koenigii* are used in a ratio of between 8:1 and 1:2 by weight.

9. A method of treating a mammal in need thereof to:
inhibit excessive generation of advanced glycation end (AGE) products,
wherein the method consists essentially of administering to the mammal an herbal composition, comprising:
an extract of *Moringa oleifera* leaves prepared by extraction with water, an alcohol, or a mixture thereof,
an extract of *Murraya koenigii* leaves prepared by extraction with water, an alcohol, or a mixture thereof, and
an extract of *Curcuma longa*,
wherein the extract of *Moringa oleifera* and the extract of *Murraya koenigii* are used in a ratio of between 8:1 and 1:2 by weight;
wherein the extract of *Curcuma longa* is prepared by a process consisting of only one or more extraction steps of *Curcuma longa* rhizome with aqueous ethanol.

10. The method of claim 9, wherein the extract of *Murraya koenigii* and the extract of *Curcuma longa* are used in a ratio of between 7:1 and 1:1 by weight.

11. The method of claim 1, wherein the herbal composition is administered in a dosage form, wherein the dosage form is selected from the group consisting of a dry powder, a liquid form, a dietary supplement, drops, a food product, a tablet, a capsule, and a controlled release tablet.

12. The method of claim 11, wherein the dosage form is a controlled release tablet having a controlled release polymeric coating.

13. The method of claim 11, wherein the dosage form is a liquid form, and the liquid form is a beverage selected from the group consisting of a tea, a soft drink, a juice, milk, coffee, and a lactic acid bacteria beverage.

14. The method of claim 11, wherein the dosage form is a solid or semisolid form, and the solid or semisolid form is a food product selected from the group consisting of a chocolate bar, a nutritional bar, a semisolid cream, a semisolid jam, a semisolid gel, a candy, a soft chewable candy, a chewing gum, a gummy candy, yoghurt, ice cream, pudding, soft adzuki bean jelly, a jelly, a cookie, a cereal, and a snack bar.

15. The method of claim 1, wherein the herbal composition comprises:
from 30% to 80% by weight of the extract of *Moringa oleifera*,
from 10% to 60% by weight of the extract of *Murraya koenigii*, and
from 5% to 20% by weight of the extract of *Curcuma longa*.

16. The method of claim 1, wherein the method is effective in treating a condition selected from the group consisting of diabetes, retinopathy, nephropathy, neuropathy, cardiomyopathy, rheumatoid arthritis, osteoporosis, cancer and an age-related neurodegenerative disease.

17. The method of claim 1, wherein the method of inhibiting excessive generation of AGE products in the mammal additionally increases lean body mass and brown adipose tissue in the mammal.

18. The method of claim 1, wherein the method of inhibiting excessive generation of AGE products in the mammal additionally converts white adipose tissue (WAT) to brown adipose tissue (WAT).

19. The method of claim 17, wherein the method of inhibiting excessive generation of AGE products in the mammal additionally converts white adipose tissue (WAT) to brown adipose tissue (WAT).

20. The method of claim 9, wherein the method of treating the mammal to inhibit excessive generation of AGE products additionally serves to a) increase lean body mass and brown adipose tissue, and/or b) convert the white adipose tissue (WAT) to brown adipose tissue (WAT).

21. The method of claim 9, wherein the extract of *Moringa oleifera* and the extract of *Curcuma longa* are used in a ratio of between 2:1 and 12:1 by weight.

* * * * *

UNITED STATES PATENT AND TRADEMARK OFFICE
CERTIFICATE OF CORRECTION

PATENT NO. : 12,070,481 B2
APPLICATION NO. : 16/756757
DATED : August 27, 2024
INVENTOR(S) : Ganga Raju Gokaraju et al.

Page 1 of 1

It is certified that error appears in the above-identified patent and that said Letters Patent is hereby corrected as shown below:

In the Claims

In Claim 1, Column 22, Lines 9-12, delete "wherein the extract of Curcuma longa is prepared by a process consisting of only one or more extraction steps of Curcuma longa rhizome with aqueous ethanol" and insert therefore --wherein the extract of Curcuma longa is prepared by a process consisting of only one or more extraction steps of extracting a Curcuma longa rhizome with aqueous ethanol--.

In Claim 9, Column 23, Lines 19-22, delete "wherein the extract of Curcuma longa is prepared by a process consisting of only one or more extraction steps of Curcuma longa rhizome with aqueous ethanol" and insert therefore --wherein the extract of Curcuma longa is prepared by a process consisting of only one or more extraction steps of extracting a Curcuma longa rhizome with aqueous ethanol--.

Signed and Sealed this
Twenty-second Day of October, 2024

Katherine Kelly Vidal
*Director of the United States Patent and Trademark Office*